(12) United States Patent
Kawabata et al.

(10) Patent No.: US 10,143,891 B2
(45) Date of Patent: Dec. 4, 2018

(54) EXERCISE ASSISTANCE APPARATUS, EXERCISE ASSISTANCE METHOD, AND EXERCISE ASSISTANCE PROGRAM

(71) Applicant: OMRON HEALTHCARE CO., LTD., Muko-shi, Kyoto (JP)

(72) Inventors: Yasuhiro Kawabata, Muko (JP); Nina Shen, Kyoto (JP); Kengo Nishiyama, Muko (JP); Reiji Fujita, Muko (JP); Yuki Yamashita, Muko (JP); Toshimichi Murai, Muko (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 0 days.

(21) Appl. No.: 15/812,687

(22) Filed: Nov. 14, 2017

(65) Prior Publication Data

US 2018/0093134 A1     Apr. 5, 2018

Related U.S. Application Data

(63) Continuation of application No. PCT/JP2016/064482, filed on May 16, 2016.

(30) Foreign Application Priority Data

May 26, 2015   (JP) .................................. 2015-106850

(51) Int. Cl.
*G08B 23/00*       (2006.01)
*A63B 24/00*       (2006.01)
(Continued)

(52) U.S. Cl.
CPC ...... *A63B 24/0087* (2013.01); *A63B 24/0062* (2013.01); *A63B 69/00* (2013.01);
(Continued)

(58) Field of Classification Search
CPC ........ A63B 24/0062; A63B 2424/0093; A63B 71/0686; A63B 24/0087; A61B 5/7278; A61B 5/11; A61B 5/742
(Continued)

(56) References Cited

U.S. PATENT DOCUMENTS

| 2003/0078138 | A1* | 4/2003 | Toyama | A63B 22/0242 482/8 |
| 2008/0096726 | A1* | 4/2008 | Riley | A63B 24/0006 482/8 |
| 2017/0225057 | A1* | 8/2017 | Takano | A63B 71/0686 |

FOREIGN PATENT DOCUMENTS

| JP | H07-213499 A | 8/1995 |
| JP | H08-052120 A | 2/1996 |

(Continued)

OTHER PUBLICATIONS

Jul. 19, 2016 International Search Report submitted within International Patent Application No. PCT/JP2016/064482.

*Primary Examiner* — Toan N Pham
(74) *Attorney, Agent, or Firm* — Oliff PLC (57) ABSTRACT

An exercise assistance apparatus, an exercise assistance method, and an exercise assistance program, according to which it is possible to cause a user to perform exercise at an appropriate load. An exercise assistance apparatus includes: a pulse measurement unit that measures a pulse rate of a user, a movement pace measurement unit that measures a movement pace of the user and a guide unit that guides the movement pace of the user based on a pulse rate range set in advance by the user, the pulse rate measured by the pulse measurement unit, and the movement pace measured by the movement pace measurement unit.

4 Claims, 5 Drawing Sheets

(51) Int. Cl.
*A63B 69/00* (2006.01)
*A63B 71/06* (2006.01)

(52) U.S. Cl.
CPC .......... *A63B 71/06* (2013.01); *A63B 71/0619* (2013.01); *A63B 2024/0093* (2013.01); *A63B 2071/065* (2013.01); *A63B 2230/067* (2013.01)

(58) Field of Classification Search
USPC .......................... 340/573.1, 539.12; 482/8, 9
See application file for complete search history.

(56) References Cited

FOREIGN PATENT DOCUMENTS

| | | |
|---|---|---|
| JP | 2001-218745 A | 8/2001 |
| JP | 2002-153430 A | 5/2002 |
| JP | 2002-177413 A | 6/2002 |
| JP | 2007-130356 A | 5/2007 |
| JP | 2008-167783 A | 7/2008 |
| JP | 2009-142333 A | 7/2009 |
| JP | 2013-223558 A | 10/2013 |

\* cited by examiner

EXERCISE ASSISTANCE APPARATUS, EXERCISE ASSISTANCE METHOD, AND EXERCISE ASSISTANCE PROGRAM

TECHNICAL FIELD

The present invention relates to an exercise assistance apparatus, an exercise assistance method, and an exercise assistance program.

BACKGROUND ART

Patent Documents 1 to 3 disclose apparatuses that assist efficient exercise by managing a pulse rate or a heart rate.

A bodily information measurement apparatus according to Patent Document 1 calculates an exercise intensity using the measured pulse rate and displays the calculated exercise intensity. The bodily information measurement apparatus changes the method of displaying the exercise intensity according to whether or not the calculated exercise intensity falls within an appropriate range, and the bodily information measurement apparatus displays advice information according to which the exercise intensity will fall within the appropriate range. The user can maintain an appropriate exercise intensity in accordance with the advice information.

The bodily information measurement apparatus disclosed in Patent Document 2 illuminates a light emitting portion with a blue color if the heart rate of the user is less than 120, illuminates the light emitting portion with a green color if the heart rate is 120 to 140, and illuminates the light emitting portion with a red color if the heart rate exceeds 140. The user can easily keep track of the state of his or her body using the state of the light emitting portion.

The bodily information measurement apparatus according to Patent Document 3 calculates an exercise amount based on the detected heart rate, and reports whether or not the calculated exercise amount is appropriate. If the calculated exercise amount exceeds an appropriate value, the bodily information measurement apparatus causes a buzzer sound to ring in long cycles, and if the calculated exercise amount falls below the appropriate value, the bodily information measurement apparatus causes the buzzer sound to ring in short cycles. The user can keep track of whether or not the exercise intensity is appropriate according to the buzzer, and thereby effective exercise is possible.

CITATION LIST

Patent Literature

Patent Document 1: JP H7-213499A
Patent Document 2: JP 2007-130356A
Patent Document 3: JP 2001-218745A

SUMMARY OF INVENTION

Technical Problem

The bodily information measurement apparatuses according to Patent Document 1 and Patent Document 3 give advice to the user so that the exercise intensity is appropriate. Specifically, advice is given to raise or lower the exercise intensity, but with this kind of simple advice, it is difficult for the user to understand the degree to which the exercise intensity is to be raised or lowered. Accordingly, it is not easy for the user to maintain the appropriate exercise intensity.

The bodily information measurement apparatus according to Patent Document 2 reports the heart rate of the user through the light emitting portion and does not give exercise advice to the user.

The present invention was made in view of the foregoing circumstances and aims to provide an exercise assistance apparatus, an exercise assistance method, and an exercise assistance program that can cause a user to perform exercise at an appropriate load.

Solution to the Problem

An exercise assistance apparatus according to the present invention includes: a pulse measurement unit configured to measure a pulse rate of a user; a movement pace measurement unit configured to measure a movement pace of the user; and a guide unit configured to guide the movement pace of the user based on a pulse rate range set in advance by the user, the pulse rate measured by the pulse measurement unit, and the movement pace measured by the movement pace measurement unit.

An exercise assistance method according to the present invention includes: a pulse measurement step of measuring a pulse rate of a user; a movement pace measurement step of measuring a movement pace of the user, and a guide step of guiding the movement pace of the user based on a pulse rate range set in advance by the user, the pulse rate measured in the pulse measurement step, and the movement pace measured in the movement pace measurement step.

An exercise assistance program according to the present invention is a program for causing a computer to execute the steps of the exercise assistance method.

Advantageous Effects of the Invention

According to the present invention, it is possible to provide an exercise assistance apparatus, an exercise assistance method, and an exercise assistance program that can cause a user to perform exercise at an appropriate load.

DESCRIPTION OF EMBODIMENTS

Hereinafter, an embodiment of the present invention will be described with reference to the drawings.

Figure 1:
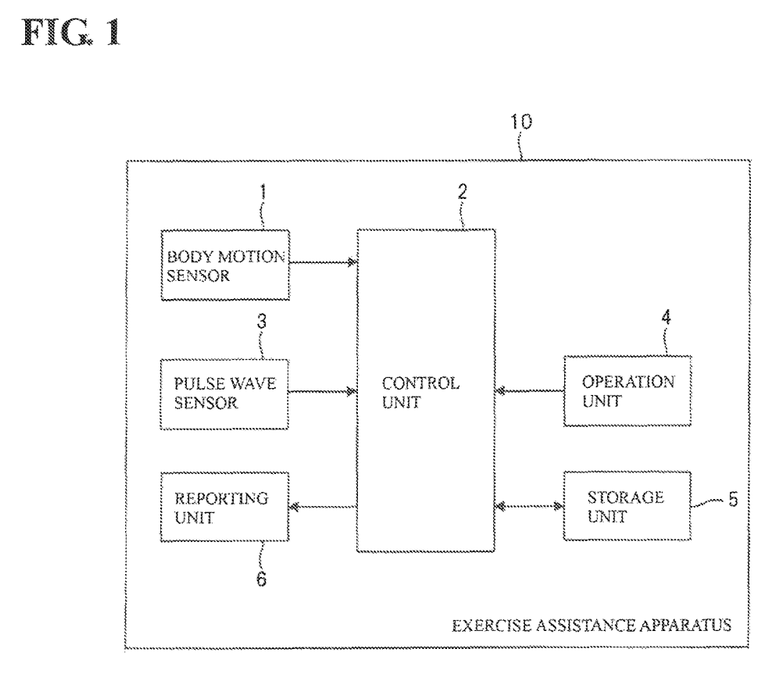
FIG. 1 is a block diagram showing a schematic configuration of an exercise assistance apparatus 10 for describing an embodiment of the present invention.

FIG. 1 is a block diagram showing a schematic configuration of an exercise assistance apparatus 10 for describing an embodiment of the present invention. Although it is envisioned that the exercise assistance apparatus 10 is of a watch type that is used while attached to the body (e.g., a wrist) of a user, there is no limitation to this.

The exercise assistance apparatus 10 includes a body motion sensor 1, a control unit 2 that performs overall control, a pulse wave sensor 3, an operation unit 4, a storage unit 5 including a storage medium such as a flash memory or a ROM (Read Only Memory), and a reporting unit 6.

The body motion sensor 1 is a sensing device for detecting information (acceleration, angular velocity, etc.) corresponding to movement of a user to which the exercise assistance apparatus 10 is attached. The body motion sensor 1 is constituted by an acceleration sensor, for example.

The pulse wave sensor 3 detects a pulse wave of a user to which the exercise assistance apparatus 10 is attached.

The control unit 2 is constituted mainly by a processor that executes a program stored in the ROM of the storage unit 5.

The operation unit 4 is a device for inputting various instructions to the control unit 2, and is constituted by physical buttons, a touch panel, or the like.

The storage unit 5 stores detection information detected by the body motion sensor 1 and the pulse wave sensor 3 and stores information needed for operations of the exercise assistance apparatus 10.

The reporting unit 6 is constituted by a device for performing reporting to a user. A light-emitting element, a vibration element (vibrator), a speaker, or a display element is used as this device.

Figure 2:
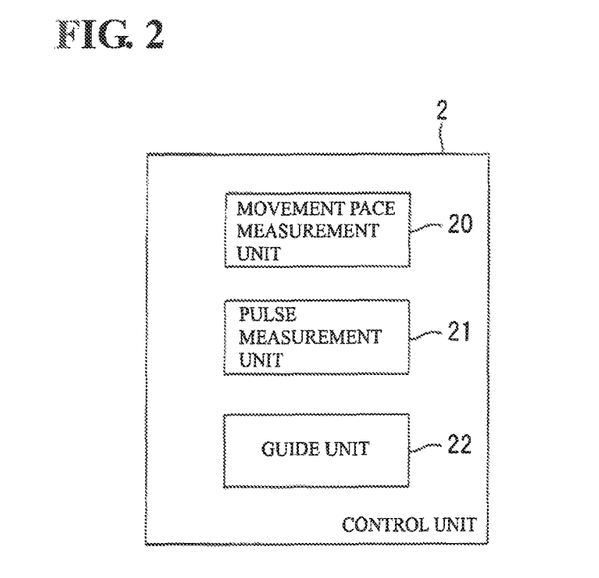
FIG. 2 is a diagram showing functional blocks realized by a control unit 2 of the exercise assistance apparatus 10 shown in FIG. 1.

FIG. 2 is a diagram showing functional blocks realized by the control unit 2 due to a processor executing a program stored in the storage unit 5 of the exercise assistance apparatus 10 shown in FIG. 1.

As shown in FIG. 2, the control unit 2 functions as a movement pace measurement unit 20, a pulse measurement unit 21, and a guide unit 22.

The movement pace measurement unit 20 measures the movement pace of the user of the exercise assistance apparatus 10 based on detection information detected by the body motion sensor 1.

"Movement pace" refers to the distance that the user moves per unit time (e.g., 1 hour), or the amount of time that it takes for the user to move a unit distance (e.g., 1 km).

Specifically, the movement pace measurement unit 20 calculates the movement distance in a predetermined period by using the step count in the predetermined period measured based on the detection information of the acceleration sensor constituting the body motion sensor 1, and the step width of the user registered in the apparatus in advance. Also, the movement distance per hour is calculated as the movement pace based on the calculated movement distance.

Here, although it is assumed that the movement pace is measured using the detection information of the body motion sensor 1, the exercise assistance apparatus 10 can be provided with a GPS (Global Positioning System) receiver and can calculate the movement pace based on a change in position information of the apparatus, received by the GPS receiver.

The pulse measurement unit 21 measures the pulse count per minute of the user based on the pulse information detected by the pulse sensor 3.

The storage unit 5 of the exercise assistance apparatus 10 stores management data for managing the exercise intensity of the user. The management data is data obtained by associating ranges of pulse rates with multiple pre-set exercise intensity levels.

Figure 3:
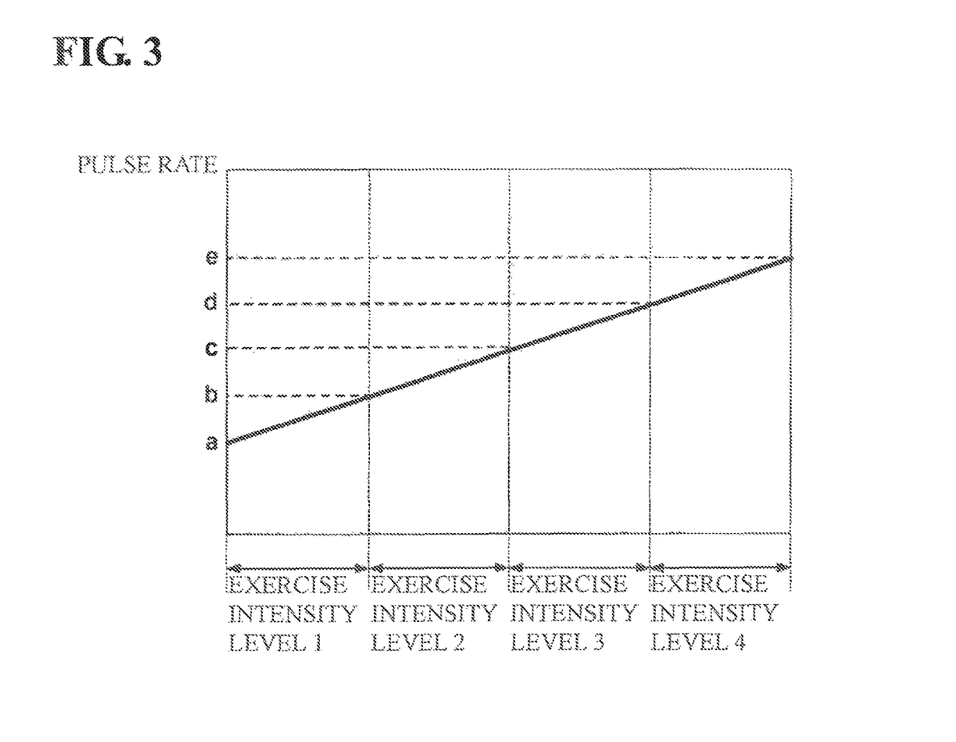
FIG. 3 is a diagram showing a relationship between exercise intensity and pulse rate.

For example, as shown in FIG. 3, the range of being greater than or equal to a pulse rate value a and less than a pulse rate value b is associated with an exercise intensity level 1. The range of being greater than or equal to a pulse rate value b and less than a pulse rate value c is associated with an exercise intensity level 2. The range of being greater than or equal to a pulse rate value c and less than a pulse rate value d is associated with an exercise intensity level 3. The range of being greater than or equal to a pulse rate value d and less than a pulse rate value e is associated with an exercise intensity level 4.

The guide unit 22 guides the movement pace of the user based on the management data stored in the storage unit 5, the pulse rate measured by the pulse measurement unit 21, and the movement pace measured by the movement pace measurement unit 20.

For example, the guidance of the movement pace is performed by causing the light-emitting element of the reporting unit 6 to flash, causing the vibration element of the reporting unit 6 to vibrate, causing a sound (e.g., a beeping sound) to be output from the speaker of the reporting unit 6, or causing the movement pace that is the guidance target to be displayed as text on the display element of the reporting unit 6, in accordance with the movement pace that is the guidance target.

The guide unit 22 references the management data read out from the storage unit 5, and controls the movement pace that is the guidance target according to whether or not the pulse rate of the user falls within the pulse rate range associated with the exercise intensity level selected by the user in advance.

Operations of the exercise assistance apparatus 10 constituted as described above will be described.

Figure 4:
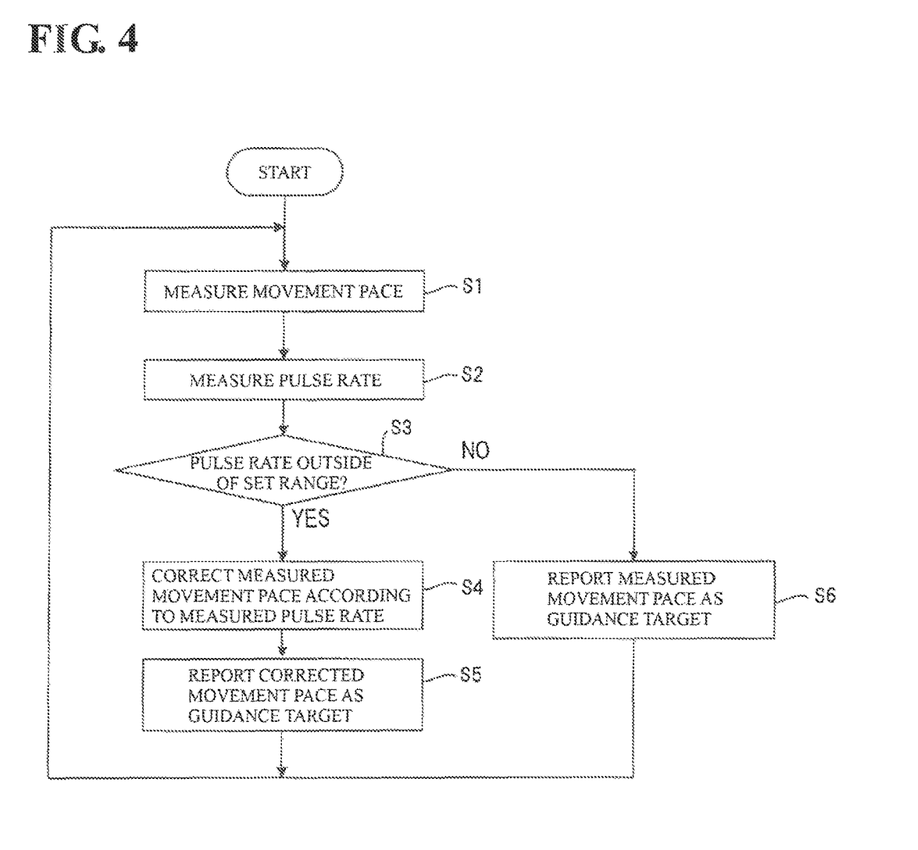
FIG. 4 is a flowchart for describing operations performed by the exercise assistance apparatus 10 shown in FIG. 1.

FIG. 4 is a flowchart for describing operations performed by the exercise assistance apparatus 10.

The control unit 2 of the exercise assistance apparatus 10 starts the processing shown in FIG. 4 when a certain exercise intensity level is selected by the user and an instruction to start a workout is given.

When the workout is started, the movement pace measurement unit 20 of the control unit 2 measures the movement pace of the user (step S1). Also, the pulse measurement unit 21 of the control unit 2 measures the pulse rate of the user (step S2).

The guide unit 22 of the control unit 2 determines whether or not the pulse rate measured by the pulse measurement unit 21 is outside of the pulse rate range (the set range) that corresponds to the exercise intensity level selected by the user (step S3).

When the result of the determination in step S3 is YES, the guide unit 22 corrects the movement pace measured in step S1 according to the pulse rate measured in step S2 (step S4).

For example, if the pulse rate measured in step S2 falls below the lower limit value of the set range of pulse rates, the guide unit 22 obtains the corrected movement pace by adding a first value to the movement pace measured in step S1.

Also, if the pulse rate measured in step S2 exceeds the upper limit value of the set range of pulse rates, the guide unit 22 obtains the corrected movement pace by subtracting the first value from the movement pace measured in step S1.

The first value used in the correction may be a fixed value that is determined in advance, but it is preferable that the first value is changed according to how far away the pulse rate measured in step S2 is from the upper limit value or the lower limit value of the set range.

Specifically, if the pulse rate measured in step S2 exceeds the upper limit value of the set range, the guide portion 22 makes the first value larger the larger the difference between the pulse rate and the upper limit value of the set range is.

Also, if the pulse rate measured in step S2 falls below the lower limit value of the set range, the guide portion 22 makes the first value larger the larger the difference between the pulse rate and the lower limit value of the set range is.

After step S4, the guide unit 22 sets the corrected movement pace as the guidance target, causes the set movement pace to be reported from the reporting unit 6 to the user, and thus guides the movement pace of the user (step S5).

Specifically, the guide unit 22 performs reporting to the user by causing the light-emitting element to flash with a rhythm that matches the set movement pace, causing the vibration element to vibrate with a rhythm that matches the set movement pace, causing a sound to be output with a rhythm that matches the set movement pace, or causing the set movement pace to be displayed as text information.

On the other hand, when the result of the determination in step S3 is NO, or in other words, if the pulse rate measured in step S2 is within the set range, the guide unit 22 sets the movement pace measured in step S1 as the guidance target as-is and causes the set movement pace to be reported from the reporting unit 6 to the user (step S6). After step S5 and step S6, the processing returns to step S1.

As described above, according to the exercise assistance apparatus 10, if the pulse rate of the user is outside of the set range set in advance by the user, the movement pace of the user is used as a reference to correct the movement pace, which is then reported to the user.

In this manner, according to the exercise assistance apparatus 10, the target movement pace can be reported to the user instead of giving the user uniform guidance such as "Please increase your movement pace" or "Please reduce your movement pace".

For this reason, the user can keep track of how much to adjust his or her current movement pace to reach the appropriate exercise intensity. Accordingly, the user can easily maintain his or her desired exercise intensity and can perform efficient exercise.

Note that the guide unit 22 may control the movement pace that is the guidance target according to whether or not the pulse rate is stable, even if the pulse rate of the user is within the set range. Hereinafter, operations according to a modified example will be described.

Figure 5:
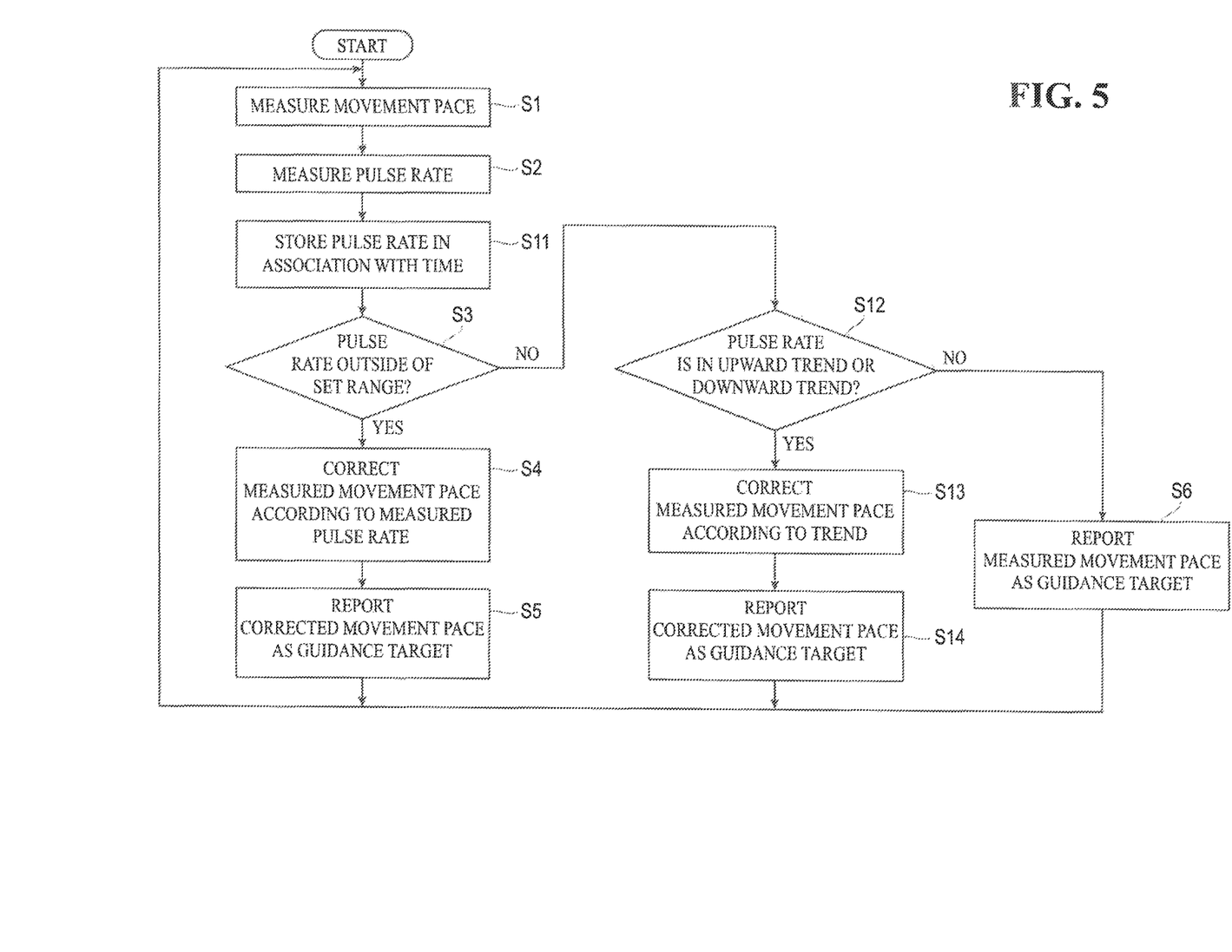
FIG. 5 is a flowchart for describing a modified example of operations performed by the exercise assistance apparatus 10 shown in FIG. 1.

FIG. 5 is a flowchart for describing a modified example of operations performed by the exercise assistance apparatus 10 shown in FIG. 1. In FIG. 5, processing that is the same as that in FIG. 4 is denoted by the same reference numerals thereas, and description thereof is not included.

When the pulse rate is measured in step S2, the control unit 2 stores the measured pulse rate in the storage unit 5 in association with the time instant (step S11).

After step S11, the processing of step S3 is performed, and if the result of the determination in step S3 is YES, the processing of step S4 and onward is performed.

When the result of the determination in step S3 is NO, the guide unit 22 determines whether or not the pulse rate of the user is in an upward trend or a downward trend (step S12).

The pulse rate being in an upward trend means, for example, that the average value of difference values (values obtained by subtracting a pulse rate at an earlier time instant from a pulse rate at a later time instant) at adjacent time instants of pulse rates corresponding to time instants in a period from the most recent pulse rate measurement time instant to a time point that is a pre-determined time before (hereinafter referred to as a calculation period) is a positive value and is greater than or equal to a first threshold value (a positive value).

The pulse rate being in a downward trend means that, for example, the average value is a negative value and is less than or equal to a second threshold value (a negative value).

Alternatively, an approximation line may be obtained using the least squares method for the pulse rate corresponding to the time instants in the calculation period, and if the slope of the approximation line is positive and is greater than or equal to a threshold value (a positive value), it may be determined that the pulse rate is in an upward trend, and if the slope of the approximation line is negative and is less than or equal to a threshold value (a negative value), it may be determined that the pulse rate is in a downward trend. It is preferable to use 10 seconds to about 30 seconds as the calculation period.

When the average value is a positive value and is less than a first threshold value, when the average value is a negative value and is greater than a second threshold value, or when the average value is 0, it is determined that the pulse rate of the user is not in an upward trend or a downward trend, or in other words, the pulse rate is stable.

When the result of the determination of step S12 is YES, the guide unit 22 corrects the movement pace measured in step S1 according to the change trend of the pulse rate (step S13).

Specifically, if the pulse rate is in an upward trend, the guide unit 22 subtracts a second value from the movement pace measured in step S and thus performs correction so that the movement pace decreases.

Also, if the pulse rate is in a downward trend, the guide unit 22 adds the second value to the movement pace measured in step S1 and thus performs correction so that the movement pace increases.

After step S13, the guide unit 22 sets the movement pace corrected in step S13 as the guidance target, causes the set movement pace to be reported from the reporting unit 6 to the user, and thus guides the movement pace of the user (step S14). After step S14, the processing returns to step S1.

When the result of the determination in step S12 is NO, or in other words, when the pulse rate is stable, the processing of step S6 is performed, and therefore the processing returns to step S1.

As described above, according to modified example shown in FIG. 5, even if the pulse rate of the user falls within the set range, if the pulse rate is in an upward trend or a downward trend, the measured movement pace is corrected and the corrected movement pace is reported. If the pulse rate is in an upward trend or in a downward trend, it is highly likely that the pulse rate of the user will fall out of the set range in the future.

For this reason, in such a case as well, the movement pace is guided such that the upward trend or the downward trend of the pulse rate is eliminated, whereby it is easier for the user to maintain his or her desired exercise intensity, and efficient exercise can be performed.

Note that the second value used in the correction in step S13 may be a pre-determined fixed value, but it is possible to change the second value according to the degree of rising or falling of the pulse rate of the user.

The degree of rising of the pulse rate is information indicating the degree to which the pulse rate rose in the calculation period in which the average value was obtained. This information can be obtained by integrating the differences between the pulse rates in the calculation period. Alternatively, this information can also be obtained by subtracting the pulse rate corresponding to the earliest time instant from the pulse rate corresponding to the most recent time instant in the calculation period.

The degree of falling of the pulse rate is information indicating the degree to which the pulse rate fell in the calculation period in which the average value was obtained. This information can be obtained by integrating the differences between the pulse rates in the calculation period. Alternatively, this information can also be obtained by subtracting the pulse rate corresponding to the earliest time instant from the pulse rate corresponding to the most recent time instant in the calculation period.

In the case of using the method of obtaining the approximation lines, the degree of rising of the pulse rate and the degree of falling of the pulse rate can be set to be the sizes of the slopes of the approximation lines.

The guide unit 22 need only make the second value larger the larger the degree of rising or the degree of falling of the pulse rate of the user is.

By making the second value variable in this way, there is a possibility that the amount of time from when the result of the determination in step S12 is YES to when the result of the determination in step S12 is NO can be shortened more than in the case where the second value is fixed. For this reason, the exercise intensity can be returned to the appropriate direction at an early stage, and efficient exercise of the user can be supported.

In the case where the first value used in the correction in step S4 is made variable as well, similarly, the exercise intensity can be returned to an appropriate intensity at an early stage, and efficient exercise of the user can be supported.

As described above, examples of methods for reporting the guidance target for the movement pace include a method of causing a light-emitting element to flash with a period corresponding to the guidance target, a method of causing a vibration element to vibrate with a period corresponding to the guidance target, and a method of causing a sound to be output from a speaker with a period corresponding to the guidance target.

Here, the reported guidance target is a movement pace, and the movement pace is a movement distance per unit time. Also, the movement distance of the user is determined according to the product of the step count and the step width. For example, a user with a step width of 80 cm and a movement pace of 80 m/min takes 100 steps per minute and advances 1 step every (60/100) seconds.

In view of this, if the movement pace that is the guidance target is 80 m/min and step width of the user is 80 cm, the guide unit 22 causes the light-emitting element to flash with a period of (60/100) seconds, which is the movement time interval per step, causes the vibration element to vibrate with a period of (60/100) seconds, or causes a sound to be emitted from the speaker with a period of (60/100) seconds. In this manner, by reporting the timing each time one step is taken, it is possible to perform guidance that is easily understood by the user.

Figure 6:
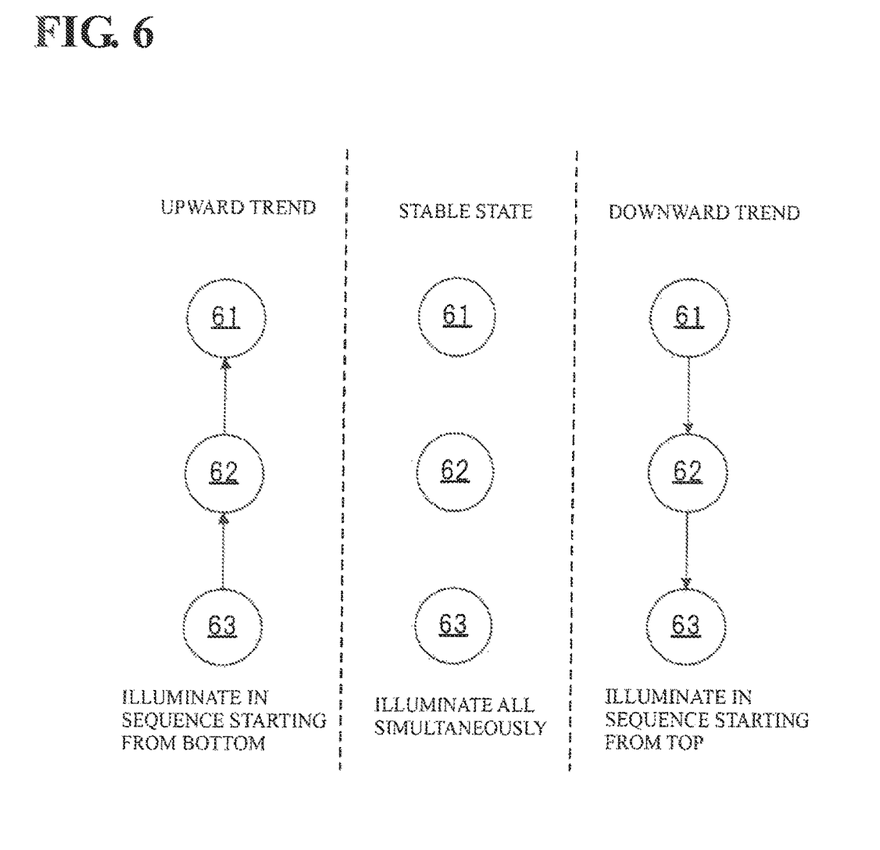
FIG. 6 is a diagram for describing a reporting method performed by a reporting unit 6 of the exercise assistance apparatus 10 shown in FIG. 1.

FIG. 6 is a diagram for illustrating a specific method for movement pace reporting processing. Here, an example of using three light-emitting elements (e.g., LEDs) 61, 62, and 63 as the reporting unit 6 will be described. With the three light-emitting elements 61, 62, and 63 constituting the reporting unit 6, in the state in which the exercise assistance apparatus 10 is attached to the wrist, the light-emitting element 61 is arranged on the user's pinky finger side and the light-emitting element 63 is arranged on the user's thumb side.

The guide unit 22 sets the following three patterns as light emission patterns of the light-emitting elements 61, 62, and 63.

The first pattern repeats a pattern of sequentially illuminating the light-emitting element 63, the light-emitting element 62, and the light-emitting element 61 in the stated order, as indicated on the left end of FIG. 6. The second pattern repeats a pattern of illuminating all of the light-emitting element 63, the light-emitting element 62, and the light-emitting element 61 simultaneously and thereafter extinguishing them, as indicated in the center of FIG. 6. The third pattern repeats a pattern of sequentially illuminating the light-emitting element 61, the light-emitting element 62, and the light-emitting element 63 in the stated order, as indicated on the right end of FIG. 6.

Also, the guide unit 22 sets one period from when the light-emitting element 63 is illuminated to when the light-emitting element 63 is next illuminated in the first pattern to be a value that matches the movement pace to be reported as the guidance target (e.g., the movement time per step).

Similarly, the guide unit 22 sets one period from when the light-emitting element 61, the light-emitting element 62, and the light-emitting element 63 are simultaneously illuminated to when the light-emitting element 61, the light-emitting element 62, and the light-emitting element 63 are next illuminated in the second pattern to be a value that matches the movement pace to be reported as the guidance target (e.g., the movement time per step).

Similarly, the guide unit 22 sets one period from when the light-emitting element 61 is illuminated to when the light-emitting element 61 is next illuminated in the third pattern to be a value that matches the movement pace to be reported as the guidance target (e.g., the movement time per step).

Then, if it is determined that the pulse rate is in an upward trend in the determination of step S12 in FIG. 5, the guide unit 22 causes the reporting unit 6 to operate in the first pattern, and furthermore, in step S13, the period of the first pattern is corrected according to the upward trend, and the reporting unit 6 is caused to operate in the first pattern with the corrected period. Accordingly, the user can understand that his or her pulse rate is in an upward trend due to the illumination pattern of the light-emitting elements and can adjust his or her walking speed in accordance with the repetition period of the first pattern.

Also, if it is determined that the pulse rate is in a downward trend in the determination of step S12 in FIG. 5, the guide unit 22 causes the reporting unit 6 to operate in a third pattern, and furthermore, in step S13, the guide unit 22 corrects the period of the third pattern according to the downward trend and causes the reporting unit 6 to operate with the third pattern with the corrected period. Accordingly, the user can understand that his or her pulse rate is in a downward trend due to the illumination pattern of the light-emitting elements and can adjust his or her walking speed in accordance with the repetition period of the third pattern.

Also, when the result of the determination in step S12 in FIG. 5 is NO, the guide unit 22 causes the reporting unit 6 to operate with a second pattern in which the period is set to be a value that corresponds to the movement pace measured in step S1. Accordingly, the user can understand that his or her pulse rate is stable due to the illumination pattern of the light-emitting elements and can maintain his or her walking speed in accordance with the repetition period of the second pattern.

A program for causing a computer to execute the steps of the flowcharts shown in FIGS. 4 and 5, or a program for causing a computer to function as the functional blocks shown in FIG. 2 can be provided by being recorded in a computer-readable non-transitory recording medium.

Examples of this kind of "computer-readable recording medium" include optical media such as CD-ROMs (Compact Disc-ROMs) and magnetic recording media such as memory cards. Also, this kind of program can be provided through downloading via a network.

The embodiments disclosed herein are to be thought of as being in all ways exemplary and not limiting. The scope of the present invention is indicated not by the description but by the claims, and meanings equivalent with the claims and all changes within the scope are intended to be included therein.

As described above, the following items are disclosed in the present description.

The disclosed exercise assistance apparatus includes: a pulse measurement unit configured to measure a pulse rate of a user; a movement pace measurement unit configured to measure a movement pace of the user; and a guide unit configured to guide the movement pace of the user based on a pulse rate range set in advance by the user, the pulse rate measured by the pulse measurement unit, and the movement pace measured by the movement pace measurement unit.

With the disclosed exercise assistance apparatus, if the pulse rate measured by the pulse measurement unit is outside of the range, the guide unit guides the movement pace by correcting the movement pace measured by the movement pace measurement unit according to the pulse rate and reporting the corrected movement pace.

With the disclosed exercise assistance apparatus, if the pulse rate measured by the pulse measurement unit is within the range, the guide unit guides the movement pace by reporting the movement pace measured by the movement pace measurement unit.

With the disclosed exercise assistance apparatus, if the pulse rate measured by the pulse measurement unit is within the range and is in an upward trend, the guide unit guides the movement pace by correcting the movement pace measured by the movement pace measurement unit so that the movement pace decreases and reporting the corrected movement pace, if the pulse rate measured by the pulse measurement unit is within the range and is in a downward trend, the guide unit guides the movement pace by correcting the movement pace measured by the movement pace measurement unit so that the movement pace increases and reporting the corrected movement pace, and if the pulse rate measured by the pulse measurement unit is within the range and is stable, the guide unit guides the movement pace by reporting the movement pace measured by the movement pace measurement unit.

With the disclosed exercise assistance apparatus, if the pulse rate measured by the pulse measurement unit is within the range and is in an upward trend, the guide unit corrects the movement pace measured by the movement pace measurement unit to be smaller the greater the degree of rising of the pulse rate is, and if the pulse rate measured by the pulse measurement unit is within the range and is in a downward trend, the guide unit corrects the movement pace measured by the movement pace measurement unit to be greater the greater the degree of falling of the pulse rate is.

With the disclosed exercise assistance apparatus, the guide unit guides the movement pace of the user by illuminating a light-emitting element, causing a vibration element to vibrate, or causing a sound to be output from a speaker, at a movement time interval per step calculated based on the movement pace to be reported and a step width of the user.

The disclosed exercise assistance method includes: a pulse measurement step of measuring a pulse rate of a user; a movement pace measurement step of measuring a movement pace of the user, and a guide step of guiding the movement pace of the user based on a pulse rate range set in advance by the user, the pulse rate measured in the pulse measurement step, and the movement pace measured in the movement pace measurement step.

The disclosed exercise assistance program is a program for causing a computer to execute the steps of the exercise assistance method.

INDUSTRIAL APPLICABILITY

According to the present invention, it is possible to provide an exercise assistance apparatus, an exercise assistance method, and an exercise assistance program that can cause a user to perform exercise at an appropriate load.

Although the present invention was described above through specific embodiments, the present invention is not limited to the embodiments and various modifications are possible without departing from the technical idea of the disclosed invention.

The present application claims priority based on Japanese Patent Application No. 2015-106850 filed on May 26, 2015, the contents of which are incorporated herein.

REFERENCE SIGNS LIST

1 Body motion sensor
2 Control unit
3 Pulse wave sensor
4 Operation unit
5 Storage unit
6 Reporting unit
10 Exercise assistance apparatus
20 Movement pace measurement unit
21 Pulse measurement unit
22 Guide unit
61, 62, 63 Light-emitting element

The invention claimed is:

1. An exercise assistance apparatus comprising:
a pulse measurement unit configured to measure a pulse rate of a user;
a movement pace measurement unit configured to measure a movement pace of the user; and
a guide unit configured to guide the movement pace of the user based on a pulse rate range set in advance by the user, the pulse rate measured by the pulse measurement unit, and the movement pace measured by the movement pace measurement unit,
wherein if the pulse rate measured by the pulse measurement unit is outside of the range, the guide unit guides the movement pace by correcting the movement pace measured by the movement pace measurement unit according to the pulse rate and reporting the corrected movement pace, and
furthermore, if the pulse rate measured by the pulse measurement unit is within the range and is in an upward trend, the guide unit guides the movement pace by correcting the movement pace measured by the movement pace measurement unit so that the movement pace is smaller the greater the degree of rising of the pulse rate is and reporting the corrected movement pace, if the pulse rate measured by the pulse measurement unit is within the range and is in a downward trend, the guide unit guides the movement pace by correcting the movement pace measured by the movement pace measurement unit so that the movement pace is greater the greater the degree of falling of the pulse rate is and reporting the corrected movement pace, and if the pulse rate measured by the pulse measurement unit is within the range and is stable, the guide unit guides the movement pace by reporting the movement pace measured by the movement pace measurement unit.

2. The exercise assistance apparatus according to claim 1, wherein the guide unit guides the movement pace of the user by illuminating a light-emitting element, causing a vibration element to vibrate, or causing a sound to be output from a speaker, at a movement time interval per step calculated based on the movement pace to be reported and a step width of the user.

3. An exercise assistance method comprising:

a pulse measurement step of measuring a pulse rate of a user;

a movement pace measurement step of measuring a movement pace of the user; and a guide step of guiding the movement pace of the user based on a pulse rate range set in advance by the user, the pulse rate measured in the pulse measurement step, and the movement pace measured in the movement pace measurement step, wherein in the guide step, if the pulse rate measured in the pulse measurement step is outside of the range, the movement pace is guided by correcting the movement pace measured in the movement pace measurement step according to the pulse rate and reporting the corrected movement pace, and furthermore, if the pulse rate measured in the pulse measurement step is within the range and is in an upward trend, the movement pace is guided by correcting the movement pace measured in the movement pace measurement step so that the movement pace is smaller the greater the degree of rising of the pulse rate is and reporting the corrected movement pace, if the pulse rate measured in the pulse measurement step is within the range and is in a downward trend, the movement pace is guided by correcting the movement pace measured in the movement pace measurement step so that the movement pace is greater the greater the degree of falling of the pulse rate is and reporting the corrected movement pace, and if the pulse rate measured in the pulse measurement step is within the range and is stable, the movement pace is guided by reporting the movement pace measured in the movement pace measurement step.

4. An exercise assistance program for causing a computer to execute the steps of the exercise assistance method according to claim 3.

* * * * *